United States Patent [19]

Krause et al.

[11] Patent Number: 5,284,622
[45] Date of Patent: Feb. 8, 1994

[54] TEST CARRIER FOR THE ANALYSIS OF FLUIDS

[75] Inventors: Manfred Krause, Viernheim; Gerd K. P. Schafer, Ludwigshafen, both of Fed. Rep. of Germany

[73] Assignee: Boehringer Mannheim GmbH, Mannheim, Fed. Rep. of Germany

[21] Appl. No.: 953,050

[22] Filed: Sep. 30, 1992

[30] Foreign Application Priority Data

Oct. 2, 1991 [DE] Fed. Rep. of Germany ....... 4132743

[51] Int. Cl.⁵ ................. G01N 31/00; G01N 33/03; G01N 23/00
[52] U.S. Cl. ........................ 422/60; 422/55; 422/56; 422/58; 422/61; 436/169; 436/170
[58] Field of Search .......... 422/55, 56, 58, 60, 422/61; 436/169, 170

[56] References Cited

U.S. PATENT DOCUMENTS

| | | | |
|---|---|---|---|
| 3,802,842 | 4/1974 | Lange et al. | 422/58 |
| 4,549,655 | 10/1985 | Forsythe, Jr. et al. | 206/59 |
| 4,668,472 | 5/1987 | Sakamoto et al. | 422/56 |
| 4,719,085 | 1/1988 | Jacobs | 422/56 |
| 4,839,297 | 6/1989 | Freitag et al. | 436/170 |
| 4,876,067 | 10/1989 | Deneke et al. | 422/56 |
| 4,877,586 | 10/1989 | Devaney, Jr. et al. | 422/101 |
| 4,912,034 | 3/1990 | Kalra et al. | 435/7 |
| 5,071,746 | 12/1991 | Wilk et al. | 435/7.94 |
| 5,104,811 | 4/1992 | Berger et al. | 436/164 |
| 5,130,258 | 7/1992 | Makino et al. | 436/169 |
| 5,132,208 | 7/1992 | Freitag et al. | 435/7.1 |
| 5,167,924 | 12/1992 | Clark | 422/58 |
| 5,173,261 | 12/1992 | Krause et al. | 422/58 |
| 5,188,966 | 2/1993 | Eikmeier et al. | 436/170 |

FOREIGN PATENT DOCUMENTS

| | | |
|---|---|---|
| 0119623 | 9/1984 | European Pat. Off. |
| 0452740A1 | 10/1991 | European Pat. Off. |
| 3523439 | 1/1987 | Fed. Rep. of Germany |
| 9116626 | 10/1991 | World Int. Prop. O. |

Primary Examiner—James C. Housel
Assistant Examiner—N. Bhat
Attorney, Agent, or Firm—Nikaido, Marmelstein, Murray & Oram

[57] ABSTRACT

A test carrier for the analysis of fluids has a test field which is held in a frame and a test application surface for the application of a sample fluid. Sometimes called an "analysis chip", such devices are suitable for accommodating a test layer pack which has a plurality of layers lying loosely on one another. These devices are thin and allow for low cost manufacturing and simple and efficient handling, and has a base body of a plastic material, with a trough-shaped depression for accommodating the test field therein. A retaining net of a plastic material spans above the depression and the test field.

8 Claims, 2 Drawing Sheets

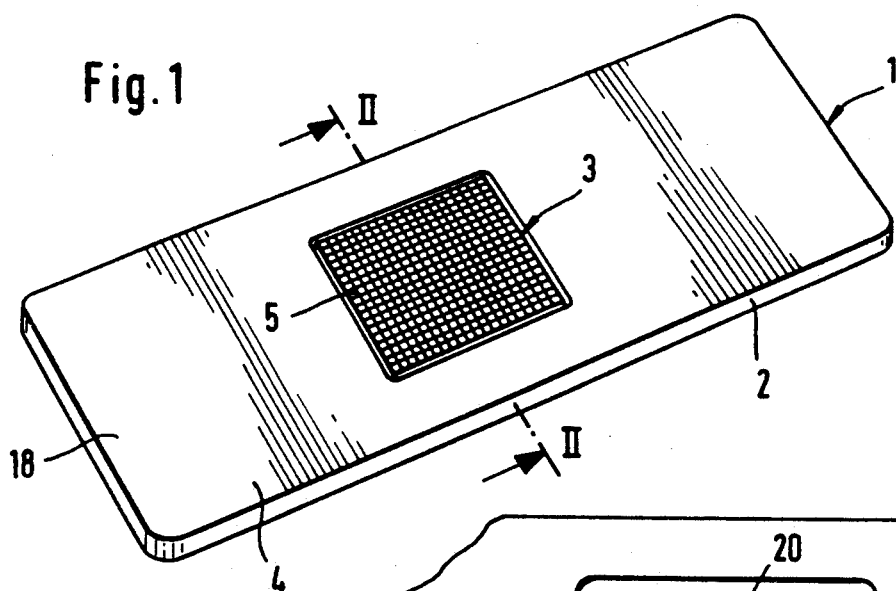
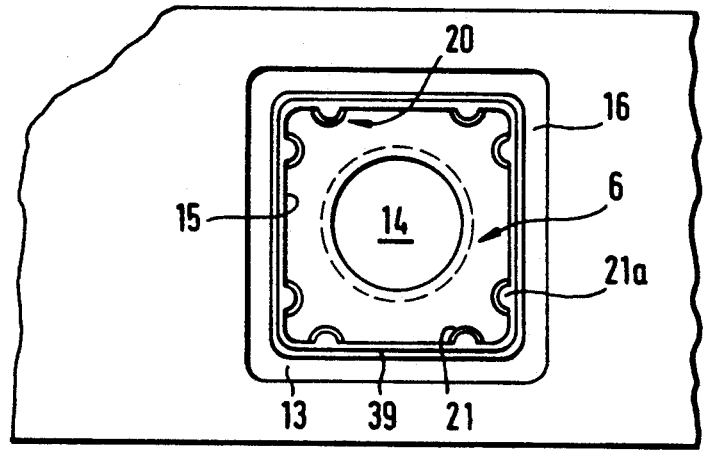
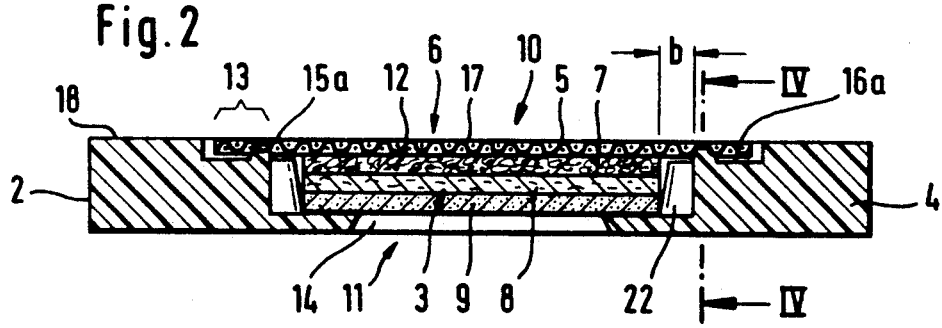
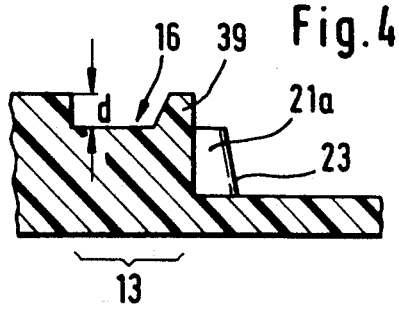
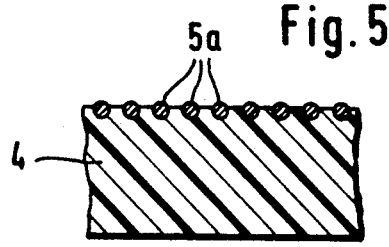

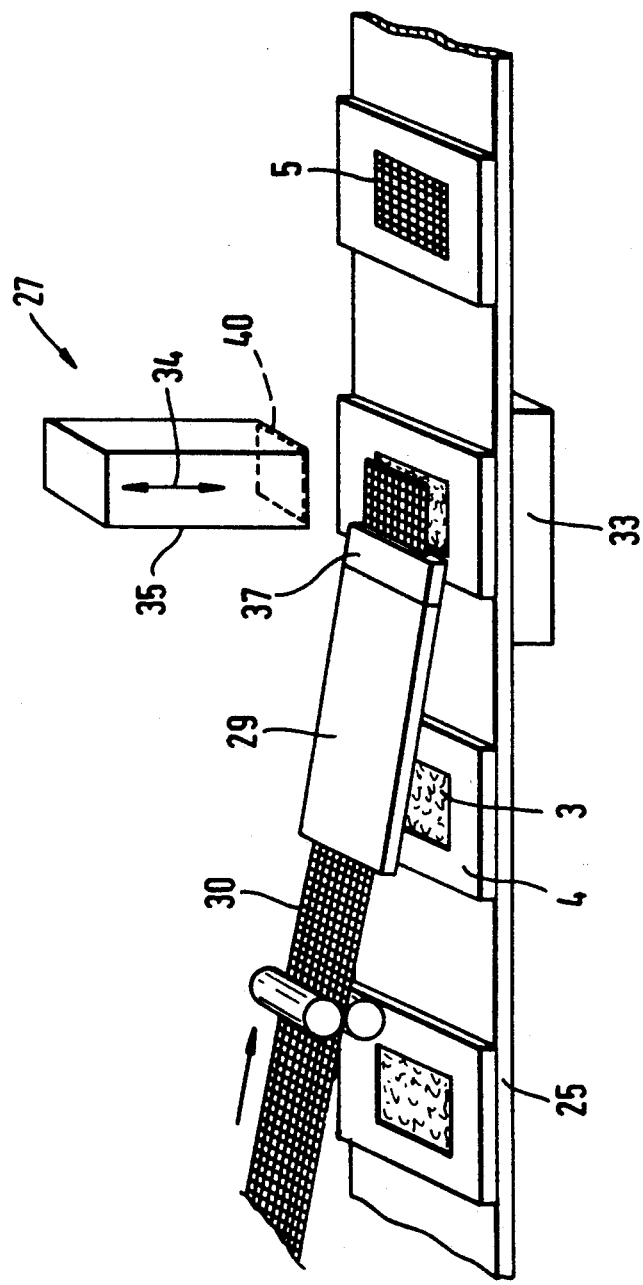

TEST CARRIER FOR THE ANALYSIS OF FLUIDS

The invention relates to a test carrier for the analysis of fluids, comprising a test field which is held in a frame and has a sample application surface for the application of a sample fluid, together with a method for manufacturing such a test carrier.

For the qualitative or quantitative analytical determination of components of fluids, in particular body fluids of humans or animals, so-called test carriers are being increasingly used. They contain the reagents required for the analysis in one or more test layers in dry form and are therefore also known in the English literature as "solid state analysis devices". The sample is applied to a sample application surface and the reaction of sample and reagents leads to a detectable signal, in particular a colour change, which can be evaluated visually or by means of an instrument, in most cases by reflection photometry.

Numerous different types of test carrier are known, which differ not only with regard to the reagents used, but also with respect to their construction, in particular as regards the arrangement and fixing of the test layers. In particular, the following two fundamentally different types of test carrier can be distinguished.

Strip-type test carriers (test strips) consist essentially of a longitudinal carrying layer of plastics material and test layers fixed onto the latter. The connection between the test layers and the plastics carrier is usually produced by bonding, the adhesion in many cases not taking place over the whole area, but only at one edge of the test layer. In some cases additional fixing means are also used, such as perforated films or nets, which are fixed to the carrying layer and secure the test layers indirectly. The test layers can with this arrangement be manufactured independently of one another and be arranged and fixed during the final assembly of the strip-type test carriers in accordance with the requirements of the respective analysis.

In the case of the second type of test carrier a test field, which contains the reagents, is held by a frame in a similar way to a photographic slide. Such test carriers will be referred to below as "test carriers with frame" or "analysis chips". In the English-language literature the term "analysis slides" is commonly used.

The test field of the test carriers with frame consists usually of a transparent carrier material, on which similarly to the light-sensitive layers of a photographic film one or more reagent layers are coated above one another, so that they are connected firmly to one another over their whole area. The test field is therefore a single part which may be framed without difficulty in a frame of plastics material or water-proof cardboard.

It can be regarded as an advantage of the analysis chips that the frame facilitates transport and positioning during the automatic carrying out of analyses by means of an apparatus. On the other hand, however, manufacture by the known methods is comparatively expensive. This applies particularly if the test field is constructed as a test layer pack consisting of at least two layers lying loosely on one another.

The aim of the invention is to provide a test carrier with frame which is also suitable for applications in which the test field is provided as a test layer pack consisting of at least two layers lying loosely on one another. The test carrier is to be distinguished at the same time by extreme thinness, ease of handling and low-cost manufacture.

The aim is achieved in the case of a test carrier of the kind described in the preamble by the fact that in a base body of plastics material a trough-shaped depression for accommodating the test field is provided and the depression is spanned above the test field by a retaining net made of a plastics material.

Such a test carrier is of extremely simple construction. The base body has a very simple form and may be manufactured simply and cost-effectively from a thermoplastic plastics material by the injection-moulding process. It may consist of a flat disc without any complicated shapes. Only the trough-shaped depression for accommodating the test field has to be engraved. It is naturally also possible, however, to provide additional recesses or other plastic shapes, which are expedient for example for transporting the analysis chip in analysis instrument or at the manufacturing stage.

As the second part of the frame there is required only the retaining net, which is only slightly bigger than the test field itself. Since it consists of a commercially available plastics fabric of preferably monofilament fibres, the material costs for the latter are extremely low.

In the context of the invention it has been found that not only does the net reliably secure a test layer pack consisting of several test layers lying substantially loosely (in any case without connection over their whole area) on one another, but the elasticity of the retaining net, which is typical of many plastics net materials, may have favourable results as regards fluid contact of the test layers with one another. Uniform fluid transfer between the test layers and hence good analytical accuracy may be achieved, whereas with rigid fixing of a test field pack the unavoidable thickness differences of the usual test fields can lead to strongly differentiated pressure loading and consequently to the non-uniform passage of fluid.

In the context of the invention it is possible to combine test layers of very different materials, depending on the requirement of the respective test, into highly varied test layer packs. For example, composite fibre structures (woven fabric or fleece), fine-pored plastics layers (membranes), film layers of porous or swellable films and test layers based on paper may be combined with one another, in order to exploit for each layer the properties advantageous in the respective application.

In the case of test strips the use of a net for covering the test fields has been known for a long time (German patent specification 2 118 455). The conditions governing the design and manufacture of test strips are however completely different from those governing analysis chips.

Test strips are manufactured in a continuous process, in which there are bonded continuously onto a plastics carrier band, whose width matches the length of the subsequent test strips, the individual test fields likewise in the form of a band (whose width corresponds to the length of the respective test field). Only at the end of the manufacturing process is the band material cut up into the individual surface strips transversely to its longitudinal direction. The fixing of the net may easily be incorporated into said manufacturing process: after the bonding-on of the test fields an additional band consisting of the net material is fed and bonded with the carrier material between the individual test layers. This procedure is also described in the German Patent specification 2 118 555, various methods commonly used for manufacturing test strips being mentioned for the fixing of the net to the carrier ribbon. The so-called "heat-sealing" method has gained acceptance in practice, in which the carrier material is provided with an adhesive layer consisting of a hot-melt adhesive and with heating of the hot-melt adhesive layer the net material is pressed into this layer by means of a heated roll.

On the other hand, test carriers with frame are manufactured individually, the frame usually consisting—as with photographic slides—of two halves of roughly equal size in their superficial dimensions. At the assembly stage the test field is introduced into the bottom half of the frame and clamped firmly or bonded firmly by the top half of the frame.

Departing from said usual method of designing analysis chips the frame is in the present invention formed essentially of only one component, namely the base body. The test field is held firmly in the trough-shaped depression by an extremely small and light-weight component, the retaining net.

There are obviously considerable problems regarding the development of a method suitable for the low-cost mass production of the analysis chips according to the invention. These are solved by the method according to the invention, in which the test field is introduced into the trough-shaped depression in the base part, a net material for the retaining net is fed as a continuous ribbon of material and in one working step the retaining net is separated from the ribbon of net material, placed above the depression and thermally bonded with the material of the base body in a surface strip adjacent to the trough-shaped depression.

The term "thermal bonding" denotes here an operation in which at least one of the materials is heated to such an extent that it softens and at the same time the two materials are pressed against one another, so that under the effect of pressure and increased temperature the two components are firmly united without the use of an adhesive material. Preferably the thermoplastic material of the base body softens at a temperature which is not critical for the dimensional stability of the material of the retaining net, i.e. leads neither to a substantial softening nor to another kind of deterioration of the net material. During the thermal bonding with the application of pressure and temperature the threads of the retaining net penetrate into the softened mass of the base body material. After cooling and solidification of the base body material they are embedded in the latter to a large extent and are reliably secured.

Such a procedure is known for other purposes. In German Patent 2 118 455 also the possibility is mentioned of the carrier layer of a test strip itself being able to act as an adhesive layer if it consists for example of polyvinyl chloride. In this case the connection to a network may apparently take place by direct welding or by pressure after swelling of the surface with a suitable solvent, such as for example methylene chloride. These theoretical considerations have not however been implemented in practice.

The fixing of the retaining net takes place in the case of the invention in a surface strip preferably surrounding completely the trough-shaped depression, said surface strip preferably being formed as a shoulder recessed with respect to the surface of the base body. In the case of the known test strips it is possible through the use of a special hot-melt adhesive material to work with far lower temperatures than in the case of the invention, in which the base body is manufactured completely from a uniform material of sufficient stability. Moreover, the sealing takes place in the case of the test strips on only two sides of the test field very rapidly on a continuously transported band by means of rotating rollers.

The invention will be explained in detail below by means of an exemplifying embodiment represented diagrammatically in the figures, where show

BRIEF DESCRIPTION OF THE DRAWINGS

FIG. 1 is a perspective view of a test carrier according to the invention;

FIG. 2 a cross-section along the line II—II in FIG. 1;

FIG. 3 a top view of a base body prior to assembly;

FIG. 4 a enlarged cross-sectional drawing similar to FIG. 2, but only of a base body prior to the compression;

FIG. 5 a cross-section along the line IV—IV in FIG. 2;

FIG. 6 a perspective overall view of the method of manufacture according to the invention.

The test carrier 1 shown in FIG. 1 has a flat frame 2 preferably less than 3 mm, particularly preferably not more than 2 mm, thick, in the middle of which a test field 3 is located. The frame 2 is formed essentially by a base body 4. The test field 3 is spanned by a retaining net 5.

Details of the composition and arrangement are shown in FIGS. 2 and 3.

The base body 4 comprises a trough-shaped depression 6, in which the test field 3 is arranged. The test field 3 is, in the preferred case shown, constructed as a test layer pack consisting of several test layers 7, 8, 9 lying loosely on one another. The layers fulfil various functions in the test procedure. For example the topmost test layer 7 may be an erythrocyte separation layer, which serves for separating out the interfering red blood corpuscles from the blood sample. For example a glass fibre mat according to U.S. Pat. No. 4 477 575 is suitable. The layer 8 may for example be a paper layer impregnated with a reagent for a preliminary reaction, while there may be used as the bottommost test layer for example a reagent film which contains a reagent system which serves for a colour change characteristic of the analysis on the underside of the layer 9 designated as the colour formation layer. Details of the test procedure have no significance for the present invention. As a rule the test procedure is however such that the sample is applied to one side of the test layer pack, which may be designated as the sample application side 10, onto a sample application surface 12, and the measurement or visual evaluation of the detection signal takes place on the opposite side of the test layer pack (detection side 11).

The retaining net is thermally bonded with the base body 4 in a surface strip 13 surrounding the trough-shaped depression 6. It is preferably—as shown—arranged on the sample application side 10 of the test field 3 formed by the test layer pack 7, 8, 9. In this case it may fulfill important additional functions. It is with expediency coloured a clearly different colour from the frame 2, in order to mark the point at which the sample (for example a drop of blood) must be applied. This represents a handling advantage particularly in the field of self-monitoring by lay people (for example diabetics). In addition the net may contribute to a uniform distribution of the sample over the sample application surface 12 of the test field, for which purpose it may with expediency be impregnated with a detergent. For the measurement of the detection signal a measurement opening 14 is provided on the detection side 11 in the base body 4.

In exceptional cases use may however also be made in the context of the invention of a reverse arrangement, in which the retaining net 5 is arranged on the detection side and the sample application takes place on the opposite side. In each case there is designated as top side of the analysis chip in the present description that side on which the retaining net 5 is applied.

The base body 4 consists of a simple flat disc of homogeneous plastics material, for example a synthetic resin like polystyrene, which is manufactured by the injection moulding process. The trough-shaped depression provided therein is limited by a wall 15. Against the top edge 15a of the wall 15 there abuts in an outward direction a peripheral shoulder 16 which completely surrounds the trough-shaped depression 6. The surface strip 13, on which the edge of the retaining net is fixed to the base body, is a part of the horizontal surface of the shoulder 16. The depth d of the shoulder 16 should correspond roughly to the thickness of the retaining net 5 or be slightly greater, so that the surface 17 of the retaining net 5 is flush with the surface 18 of the base body 4.

The surface 17 of the base body 4 does not necessarily have to be (as represented) free of interruptions, such as for example depressions or recesses. It is essential, however, that in the region of the surface strip 13 the thickness of the base body 4 is adapted to the thickness of the test layer pack 7, 8, 9 in such a way that the tensioned retaining net 5 fixes the test layers and if necessary presses them lightly together. Consequently the term "trough-shaped depression for accommodating the test field" should be understood in the sense that a flat depression within the moulded part 4 is involved, the walls 15 of said depression being roughly as high as the sum of the above-mentioned layers, so that the tensioned retaining net presses lightly against the topmost layer.

In the preferred case shown the horizontal position of the test field 3 within the trough-shaped depression 6 is not defined directly by the walls 15 of the latter. Instead, positioning means 20 are provided which in the case shown are formed by discrete limiting elements 21 in the form of semicolumn-shaped projections 21a starting from the wall 15. By means of said positioning means the test field 3 is positioned in the trough-shaped depression 6 so that it is surrounded on all sides on the major part of its periphery by a gap 22 which is preferably at least some 0.3 mm and at most some 1 mm wide.

Said measure is of particular importance if the test field consists of several layers and sample fluid has to be prevented from running down at the lateral edges of the test field pack 7, 8, 9 without passing through the test layers one after the other in their sequence from top to bottom. Since for many reactions the correct sequence of the contacting of the individual reagents or the prior reliable separation of interfering constituents is essential, the measurement result would be distorted by a "sample short-circuiting" of this kind. It has been found, surprisingly, that this may be reliably prevented in the context of the present invention, although the area of the retaining net 5 is greater than the surface of the test field 3 and the possibility may not be excluded of the sample also being applied to regions of the retaining net 5 which lie at the edge of or outside the test field 3. Preferably the area of the retaining net is only slightly greater than the area of the test field, the area of the retaining net being preferably between 150% and 500%, particularly preferably between 180% and 300%, of the area of the test field 3.

Instead of the semicolumn-shaped projections 21a other discrete limiting elements 21 may be used as positioning means, which possess for example a triangular cross-section. The contact surface of the limiting elements, with which they come into contact with the outer edge of the test layers 7, 8, 9, should be as small as possible. A form which ensures line contact is preferred. In any case the peripheral gap 22 should be interrupted by the limiting elements 21 at most over 25%, particularly preferably over less than 10%, of its length.

According to a further preferred embodiment the limiting elements 21 are formed so that their side 23 facing the test field 3 runs from bottom to top obliquely away from the test field. The spacings of the limiting elements 21 and the dimensions of the test field 3 are in addition adapted to one another in such a way that the bottom edge of the bottommost layer 9 of the test field 3 butts against the limiting element 21. In this way very accurate positioning is achieved and at the same time simple and efficient mechanical assembly is made possible. In particular the colour formation layer 9 essential for the optical evaluation is positioned very accurately, whereas the test layers 7 and 8 lying above the latter may be positioned with a certain tolerance.

FIGS. 3 to 6 serve to explain the method according to the invention and the compositional features of the test carrier which are associated with the latter.

Base bodies 4 are transported stepwise by means of a conventionally constructed transport line 25 not shown in detail. The test field 3 is introduced into the trough-shaped depression at a filling station (not shown).

After this the analysis chip is transported to the sealing station designated overall as 27. The latter comprises a feed channel 29 by means of which a band 30 is fed from a roller, an anvil 33 let into the transport line 25 and a press die 35 movable vertically upwards and downwards in the direction of the arrow 34.

The press die 35 serves at the same time for separating an appropriate piece from the band of net material 30 to form the retaining net 5. In the case shown the band of net material 30 is of the appropriate width, so that all that is required further is to separate in each case a piece of the appropriate length. This is done preferably by punching off, the front edge of the press die 35 in the transport direction of the base bodies 4 being suitably sharp-edged and interacting with a bottom blade 37 which forms the rear end of the feed channel 29 in the transport direction. Instead of the latter, use could also be made of a band of material 30 of greater width, in which case the bottom blade 37 comprises a sharp-edged recess of the size of the desired retaining net 5 and the press die 35 must be constructed sharp-edged on all sides, in order to punch an appropriate piece out of the ribbon of net material 30.

It is essential that in a working step directly after the separation of the retaining net 5 the thermal bonding takes place in the surface strip 13 of the base body, which surface strip 13 surrounds the trough-shaped depression. To this end a peripheral pressure bead 40, indicated by dashes, of corresponding width is heated at the edge of the bottom area of contact of the press die 35. It presses the edge of the retaining net 5 against the surface strip 13, in which the compression is to take place. The edge of the retaining net 5 is pressed into the softening material of the base body 4, so that the individual threads 5a are for the most part embedded in the material, as is shown in FIG. 5. In order to facilitate this, the net material should not be too dense. Preferably the spacing of the threads should be at least half as great, particularly preferably at least just as great, as the diameter of the threads.

In order further to facilitate the compression and to reduce the thermal loading of the test fields, it is advantageous if there is provided within the press strip 13 prior to the compression a peripheral bead 39 projecting upwards (FIG. 4). It should preferably be at least some 0.2 mm, particularly preferably some 0.3 to 0.4 mm, high.

What is claimed is:

1. A test carrier for the analysis of fluids, comprising:
   a flat body formed of a plastic material, said base body having a trough-shaped depression disposed in one of its faces:
   a test field disposed in said depression, said test field having a sample application surface thereon, for the application of a sample fluid; and
   a retaining net formed of a plastic material spanning said depression and said test field disposed therein.

2. A test carrier for the analysis of fluids as recited in claim 1, wherein said test field comprises a test layer pack having at least two test layers loosely therein, wherein said at least two test layers are loosely disposed in a vertical stack.

3. A test carrier as recited in claim 1, wherein said retaining net covers said sample application surface of said test field.

4. A test carrier for the analysis of fluids as recited in claim 1, wherein said base body is of a thermoplastic material which softens at a temperature which does not affect the dimensional stability of the retaining net, and said base body further comprises a surface strip adjacent to said depression, and wherein said retaining net is melted into said surface strip.

5. A test carrier for the analysis of fluids as recited in claim 4, wherein said surface strip completely surrounds said depression.

6. A test carrier according to claim 1, further comprising a rim which is disposed around a top edge of the depression, said rim being disposed in a recessed portion of the upper surface of the base body.

7. A test carrier for analysis of fluids as recited in claim 1, wherein an outer perimeter of said trough-shaped depression is larger than an outer perimeter of said test field, and wherein said base body further comprises positioning means disposed within the depression for positioning said test field in said depression wherein a gap exists on all sides of the test field, between the outer perimeter of the test field and the outer perimeter of the depression.

8. A test carrier for the analysis of fluids as recited in claim 7, wherein said gap is at least 0.3 mm and at most 1 mm wide.

* * * * *